(12) United States Patent
Abraham et al.

(10) Patent No.: US 12,709,046 B2
(45) Date of Patent: Aug. 18, 2026

(54) SYSTEM AND PROCESS FOR MANUFACTURING LASER MARKED ELASTOMER COMPONENTS

(71) Applicant: WEST PHARMACEUTICAL SERVICES, INC., Exton, PA (US)

(72) Inventors: Silji Abraham, Southfield, MI (US); David Martin, Royersford, PA (US); Jason Krizan, Ellicott City, MD (US)

(73) Assignee: West Pharmaceutical Services, Inc., Exton, PA (US)

( * ) Notice: Subject to any disclaimer, the term of this patent is extended or adjusted under 35 U.S.C. 154(b) by 407 days.

(21) Appl. No.: 17/775,244

(22) PCT Filed: Nov. 10, 2020

(86) PCT No.: PCT/US2020/059785

§ 371 (c)(1),
(2) Date: May 6, 2022

(87) PCT Pub. No.: WO2021/096832

PCT Pub. Date: May 20, 2021

(65) Prior Publication Data

US 2023/0033805 A1 Feb. 2, 2023

Related U.S. Application Data

(60) Provisional application No. 62/933,689, filed on Nov. 11, 2019.

(51) Int. Cl.
*B29C 43/58* (2006.01)
*A61M 5/315* (2006.01)
(Continued)

(52) U.S. Cl.
CPC .......... *B29C 43/58* (2013.01); *B23K 26/0006* (2013.01); *G06K 7/1443* (2013.01);
(Continued)

(58) Field of Classification Search
CPC ........... A61B 2017/00526; A61B 2017/00907; A61B 2017/00995; A61B 90/90;
(Continued)

(56) References Cited

U.S. PATENT DOCUMENTS 5,895,192 A * 4/1999 Parnell, Sr. ...... B29D 11/00067 198/468.4
9,600,694 B1 3/2017 Memering et al.
(Continued)

FOREIGN PATENT DOCUMENTS

CN 204688648 U 10/2015
CN 108364041 A 8/2018
(Continued)

OTHER PUBLICATIONS

Merriam-Webster, Robot Definition, https://www.merriam-webster.com/dictionary/robot. (Year: 2026).*

*Primary Examiner* — Xiao S Zhao
*Assistant Examiner* — Victoria Bartlett
(74) *Attorney, Agent, or Firm* — Blank Rome LLP

(57) ABSTRACT

A system for manufacturing elastomeric components is provided. The system may include a molding station having a mold configured to receive an elastomeric material, form a pad that includes a plurality of untrimmed elastomeric components, and cure the pad. The system may further include an automated marking station comprising a laser and a camera. The automated marking station may be configured to remove the cured pad from the molding station, present the cured pad to the laser to form a mark on each of the untrimmed elastomeric components, and present the cured pad to the camera to capture an image of each mark. A process for manufacturing the elastomeric components is also provided.

12 Claims, 12 Drawing Sheets

(51) Int. Cl.

| | |
|---|---|
| ***B23K 26/00*** | (2014.01) |
| ***B23K 103/00*** | (2006.01) |
| ***B29C 37/00*** | (2006.01) |
| ***B29C 43/00*** | (2006.01) |
| ***B29C 43/02*** | (2006.01) |
| ***B29K 21/00*** | (2006.01) |
| ***B29L 31/00*** | (2006.01) |
| ***G06K 7/14*** | (2006.01) |
| ***G06T 7/00*** | (2017.01) |

(52) U.S. Cl.

CPC .......... *G06T 7/0004* (2013.01); *A61M 5/315* (2013.01); *A61M 2205/6072* (2013.01); *A61M 2207/10* (2013.01); *B23K 2103/42* (2018.08); *B29C 2037/80* (2013.01); *B29C 43/003* (2013.01); *B29C 43/02* (2013.01); *B29C 2043/585* (2013.01); *B29K 2021/003* (2013.01); *B29L 2031/753* (2013.01); *G06T 2207/30108* (2013.01); *G06T 2207/30204* (2013.01)

(58) Field of Classification Search

CPC .... A61B 90/94; A61B 90/96; B23K 2103/42; B23K 26/0006; B23K 26/082; B23K 26/0853; B23K 26/352; B23K 26/355; B23K 26/359; B29L 2031/753; B29K 2021/003; A61M 2205/6072; A61M 2207/10; A61M 5/315; B29C 2037/80; B29C 2043/585; B29C 2045/0075; B29C 43/003; B29C 43/02; B29C 43/58; B29C 45/0053; G06K 7/1443; G06T 2207/30108; G06T 2207/30204; G06T 7/0004

See application file for complete search history.

(56) References Cited

U.S. PATENT DOCUMENTS

| | | | | |
|---|---|---|---|---|
| 2005/0209822 | A1 | 9/2005 | Ishiba et al. | |
| 2006/0092013 | A1* | 5/2006 | Hager | B29C 45/14065 340/539.1 |
| 2009/0166311 | A1 | 7/2009 | Claessens | |
| 2011/0204137 | A1 | 8/2011 | Scharfenort et al. | |
| 2013/0017289 | A1 | 1/2013 | Kieburg et al. | |
| 2015/0352664 | A1* | 12/2015 | Errico | B23K 26/032 219/121.76 |
| 2016/0074865 | A1 | 3/2016 | Rao et al. | |
| 2020/0405918 | A1* | 12/2020 | Nakai | A61B 1/0011 |

FOREIGN PATENT DOCUMENTS

| | | | | |
|---|---|---|---|---|
| CN | 110181035 | A | 8/2019 | |
| EP | 2 881 441 | A1 | 6/2015 | |
| JP | 2003062037 | A | 3/2003 | |
| JP | 2005286309 | A | 10/2005 | |
| JP | 2007313876 | A | 12/2007 | |
| JP | 2009167016 | A | 7/2009 | |
| JP | 2009214141 | A | 9/2009 | |
| JP | 2012179368 | A | 9/2012 | |
| WO | 2010101037 | A1 | 10/2010 | |
| WO | 2011/135398 | A1 | 11/2011 | |
| WO | 2014068664 | A1 | 8/2014 | |
| WO | 2015132905 | A1 | 9/2015 | |
| WO | WO-2019118983 | A1 * | 6/2019 | A61M 5/31513 |

* cited by examiner

SYSTEM AND PROCESS FOR MANUFACTURING LASER MARKED ELASTOMER COMPONENTS

CROSS-REFERENCE TO RELATED APPLICATIONS

This application is a National Stage of International Patent Application No. PCT/US2020/059785, filed Nov. 10, 2020, which claims priority to U.S. Provisional Patent Application No. 62/933,689, filed Nov. 11, 2019, the disclosures of which are incorporated by reference in their entirety.

FIELD OF THE INVENTION

Embodiments described herein are directed to medical device components, and particularly elastomer components, such as stoppers or plungers, seals, and the like, that are laser marked with data or other identification information, and a method and system of marking such components, particularly during multiple manufacturing steps.

BACKGROUND

Prior attempts to serialize or mark medical device components utilized radio frequency (RF) tags, labels, mold cavity identification, or surface printing. RF tags can be expensive, rigid, and difficult to apply at scale. Labels require adhesion, which can risk leachable material into a drug, and can also be difficult to apply. Mold cavity identification is not unique, can wear down over time, and can only provide limited information. Surface printing can also create leachable material, and surface morphology differences can impact sealing or machinability.

BRIEF SUMMARY

In one aspect, the present invention relates to a method for manufacturing a medical device component. The method may comprise forming a body of the medical device component, the body having a surface and being at least partially formed from a markable material having a first color; applying a film to at least a portion of the surface of the body, including at least a portion of the markable material; and after formation of the film, exposing one or more areas of the at least a portion of the markable material to laser irradiation of a predetermined wavelength to form a visible mark on the surface of the body by changing the one or more areas to a second color different from the first color.

In another aspect, the present invention relates to a medical device component comprising a body having a first surface being at least partially formed from a markable material having a first color, the markable material having a characteristic that an area exposed to laser irradiation of a predetermined wavelength of ultraviolet light changes to a second color different from the first color; a film covering at least a portion of the first surface of the body, the film having a transmittance at the predetermined wavelength of ultraviolet light of at least 5%; and a visible mark on the markable material at the first surface of the body covered by the film. The visible mark comprising one or more areas of the markable material at the first surface having the second color.

In yet another aspect, the present invention relates to method for manufacturing a medical device component. The method may comprise forming a body of the medical device component in a molding process, the body having a surface and being at least partially formed from a markable material having a first color. The method may also comprise forming a film over at least a portion of the surface of the body, including at least a portion of the markable material. In another step, the method may comprise forming a first visible mark on the surface of the body covered by the film by exposing one or more first areas of the at least a portion of the markable material to laser irradiation of a predetermined wavelength to change the one or more first areas to a second color different from the first color, the first visible mark containing or linking to first data related to the molding and/or film formation steps. In yet another step, the method may comprise washing the medical device component from the mold and forming a second visible mark on the surface of the body covered by the film by exposing one or more second areas of the at least a portion of the markable material to laser irradiation of the predetermined wavelength to change the one or more second areas to the second color, the second visible mark containing or linking to second data related to the washing step.

In yet another aspect, the present invention relates to a system for manufacturing elastomeric components. The system may comprise a molding station comprising a mold configured to receive an elastomeric material, form a pad that includes a plurality of untrimmed elastomeric components, and cure the pad. The system may further comprise an automated marking station comprising a laser and a camera. The automated marking station may be configured to remove the cured pad from the molding station, present the cured pad to a laser to form a mark on each of the untrimmed elastomeric components, and present the cured pad to the camera to capture an image of each mark.

In yet another aspect, the present invention relates to a process for manufacturing elastomeric components. The process may comprise providing an elastomeric material to a mold, molding a pad comprising the elastomeric material, the pad comprising a plurality of untrimmed elastomeric components, curing the pad, exposing a portion of the surface of each of the untrimmed elastomeric components with a laser to form a mark, and capturing an image of each of the marks.

These and other aspects of the present invention will be apparent in view of the following description.

BRIEF DESCRIPTION OF THE DRAWINGS

The foregoing summary, as well as the following detailed description, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION

Figure 1:
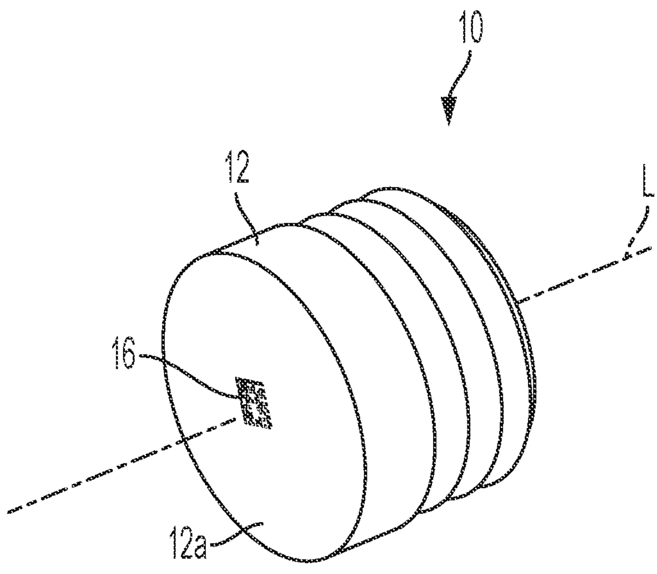
FIG. 1 is a front side perspective view of a stopper including a laser-created visible mark thereon in accordance with an embodiment of the present invention.

Certain terminology is used in the following description for convenience only and is not limiting. The words "lower," "bottom," "upper," "top," "front," "back," and "rear" designate directions in the drawings to which reference is made. The words "inwardly" and "outwardly" refer to directions toward and away from, respectively, the geometric center of the component being discussed, and designated parts thereof, in accordance with the present disclosure. Unless specifically set forth herein, the terms "a," "an," and "the" are not limited to one element, but instead should be read as meaning "at least one." "At least one" may occasionally be used for clarity or readability, but such use does not change the interpretation of "a," "an," and "the." The terminology includes the words noted above, derivatives thereof, and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

In certain aspects, by using an ultraviolet (UV) laser, drug-contact elastomer components can be marked/serialized to produce a safe, clean, and sterilization compatible product. A precise mark can be applied to a molded or finished product, even if an optional film has already been applied. This technology, particularly where the mark is created under the film, poses very little risk to the drug product, as any potentially created extractables would not be present at the surface of the component. Moreover, the technology may be preferable for components used in cryogenic applications because exposure to large temperature differentials are unlikely to substantially affect the mark, unlike labels that utilize adhesives. This technology is broadly applicable to elastomer components utilizing inorganic fillers, and can be extensible to other polymer components, especially those which can be covered in compatible films or other transparent layers.

Figure 2:
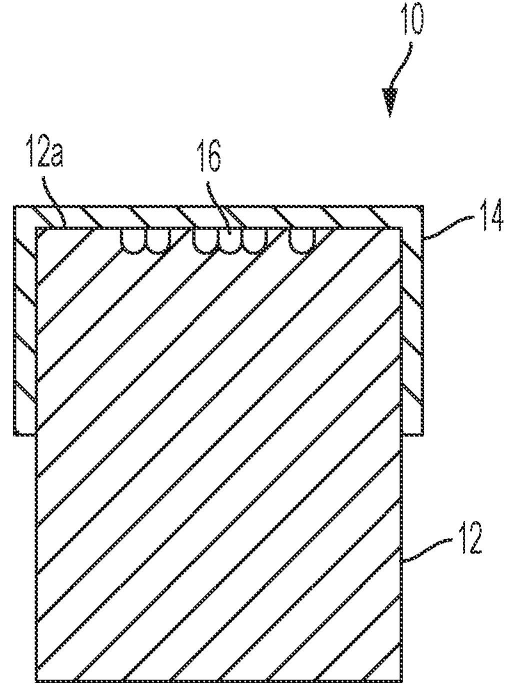
FIG. 2 is a schematic cross-sectional elevational view of a stopper including a laser-created visible mark thereon in accordance with another embodiment of the present invention.
Figure 3:
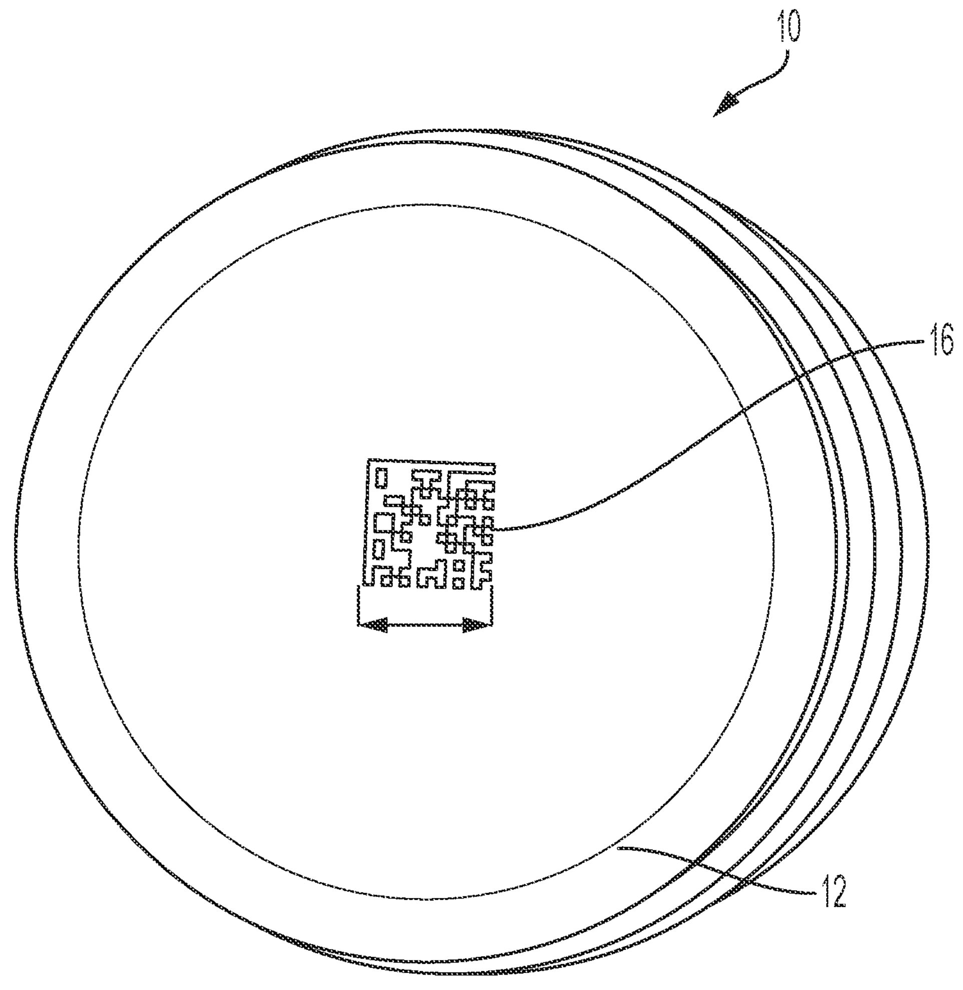
FIG. 3 is a top perspective view of a stopper including a laser-created visible mark thereon in accordance with yet another embodiment of the present invention formed thereon using a method in accordance with an embodiment of the present invention.

Referring to FIGS. 1-3, there are shown examples of a medical device component, such as a stopper 10, in accordance with various preferred embodiments. The stopper 10 includes a body 12 that is preferably formed at least partially of an elastomeric material having a first color, such as synthetic or natural rubber, e.g., butyl rubber, isoprene rubber, butadiene rubber, halogenated butyl rubber (e.g., bromobutyl rubber), ethylene propylene terpolymer, silicone rubber, ethylene propylene diene monomer (EPDM) rubber, combinations thereof, or the like, which preferably contains inorganic filler materials, such as titanium dioxide or the like. In other embodiments, the body 12 may at least partially be made from polymers having high amounts of carbon black, resulting in the first color of the body 12 material being darker. Such materials are markable, as will be explained further below. The body 12 preferably has a longitudinal axis L and a first surface 12$a$ that is oriented transverse, and more preferably, substantially perpendicular to, to the longitudinal axis L. In some embodiments, the first surface 12$a$ may come into contact with medicament. The body 12 includes additional surfaces that may be connected or adjacent to the first surface 12$a$, may extend parallel or be concentric with the longitudinal axis L, and the like. For example, the body 12 may have a cylindrical shape, such as that shown in FIG. 1, with one or more ribs concentrically formed around the longitudinal axis L for sealing the stopper 10 within a container or the like, such as a syringe (not shown).

Figure 4A:
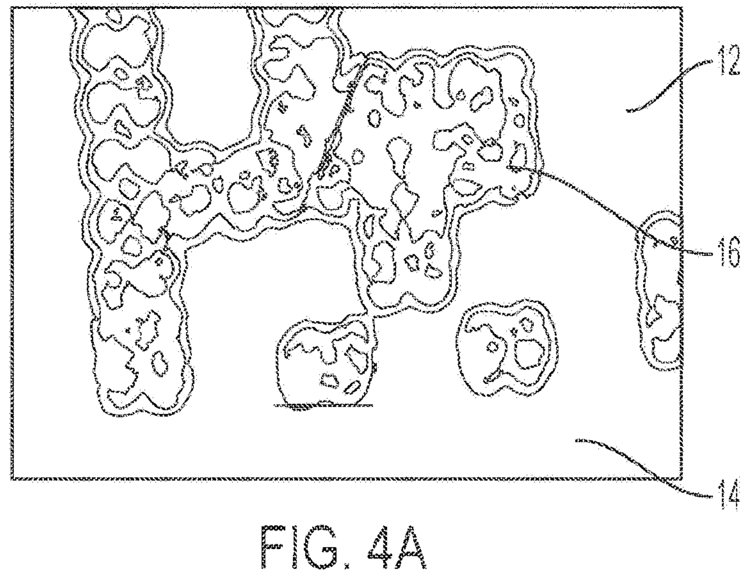
FIG. 4A is an enlarged plan view of a portion of the laser-created visible mark on the stopper of FIG. 3 with a focus at a top of an overlying film surface.

At least a portion of a surface of the body 12, and in certain embodiments preferably at least a portion of the first surface 12$a$, may be covered by a film 14 (FIGS. 2, 4A) as a barrier material between the elastomeric material of the body 12 and any medicament (not shown) with which the body 12 may come into contact. Common films 14 for such use may include, but are not limited to, materials containing tetrafluoroethylene, ethylene tetrafluoroethylene (ETFE), polytetrafluoroethylene (PTFE), perfluoroalkoxy alkanes (PFA), polyvinylidene fluoride (PVDF), fluorinated ethylene propylene (FEP), polyvinylidene fluoride (PVF), polychlorotrifluoroethylene (PCTFE), ethylene chlorotrifluoroethylene (ECTFE), perfluoroelastomer (FFPM), fluoroelastomer polymer (FPM), polyethylene (PE), cyclic olefin polymer (COP), cyclic olefin copolymer (COC), polypropylene (PP), combinations thereof, and the like.

Figure 4B:
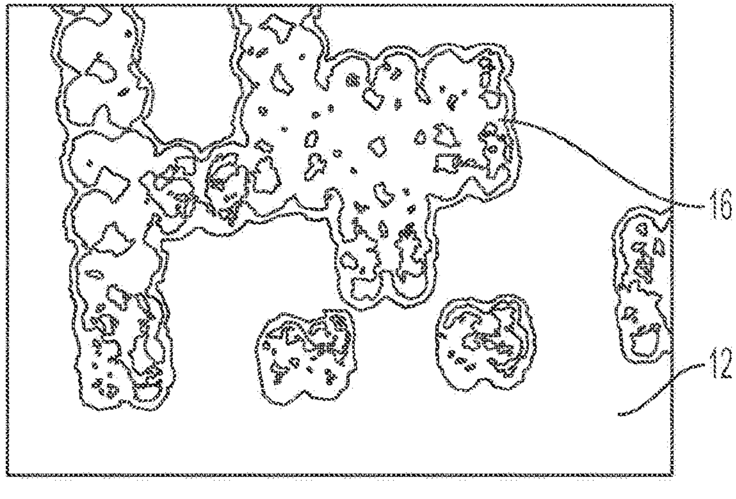
FIG. 4B is an enlarged plan view of a portion of the laser-created visible mark on the stopper of FIG. 3 with a focus on a surface of the stopper material located below the overlying film.
Figure 7:
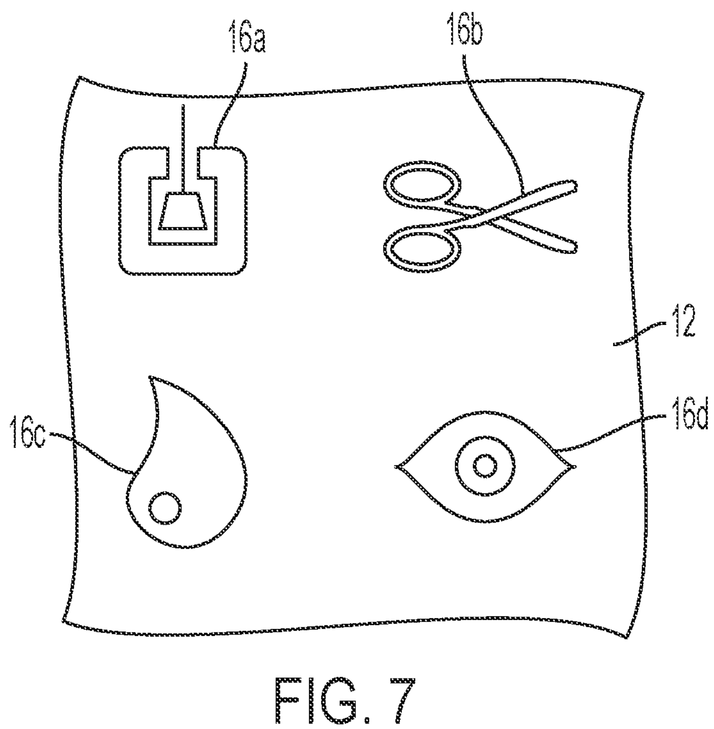
FIG. 7 is an enlarged partial top plan view of a stopper including a plurality of laser-created visible marks thereon in accordance with various embodiments of the present invention.

As shown in FIGS. 1-4B, and 7, the stopper 10 preferably includes a visible mark 16 formed on a surface of the body 12. Preferably, the visible mark 16 is formed on a surface of the body 12 that is highly visible at least during manufacture of the stopper, such as the first surface 12*a*, and may also be visible during use of the final medical device (not shown). The visible mark 16 may be at least one of machine-readable or human-readable. The visible mark 16 shown in FIGS. 3, 4A, and 4B is a Data Matrix ECC 200 code, primarily due to the code's high data density and error correcting features. However, other machine-readable codes, such as other Data Matrix codes, other two-dimensional bar codes (e.g., QR codes or the like), one-dimensional or stacked bar codes, or the like may be used. For human-readable visible marks 16, such as shown in FIG. 7, alphanumeric characters, logos, instructional images or messages, or the like can be used. The visible mark 16 can encode or provide data related to, for example, unique product or component identifiers, manufacturing data, tracking information, expiration data, use instructions, and the like. Being human-readable, readable by a smartphone or the like, or with a dedicated vision system, the stopper 10 can be tracked by manufacturers and their customers, caregivers, and/or patients.

The visible mark 16 is preferably made on a surface of the body 12 using UV laser irradiation such that one or more areas of the markable material in the body 12 exposed to the laser irradiation change to a second color different from the first color. The laser radiation is, for example, absorbed by the inorganic filler materials in the body 12, which subsequently degrade to produce a dark area. In other embodiments, such as those utilizing carbon black, the laser absorption may cause lighter areas exhibiting a "foamed" appearance. Such UV lasers are commercially available from, for example, DPSS Lasers, Inc. of Santa Clara, California. In one embodiment, the visible mark 16 can be formed using a laser (not shown) having a 355 nm wavelength, which is in the ultraviolet range. Other wavelengths and/or types of lasers, such as $CO_2$ lasers or the like, can be used as well, depending on the material of the body 12 that is sought to be marked. The process is non-contact, and generates few, if any particles.

As previously mentioned, the laser may use a mirror (not shown) to raster across the surface of the body 12 to form the visible mark 16. In another method, an XY carriage may be used to translate a laser over the portion of the surface of the body 12 to which the visible mark 16 will be applied. In yet another method, a mask having a plurality of openings may be applied to the surface of the body 12 prior to irradiating the surface with a laser. The openings may be arranged, such that upon removal of the mask, the desired visible mark 16 is left on the surface of the body 12. Laser parameters, such as power, speed, spot size, and the like may be optimized to achieve the desired effect in the visible mark 16. In addition, the stopper 10 can be stationary during the marking process, or may be in motion, such as on a production line, during marking.

As would be appreciated by one of skill in the art, dimensions of the marks and the cells (squares representing a "bit" of the code) incorporated into the various embodiments of the present invention are not limited. For example, as computing power of devices increases with every new generation of technology, the complexity and number of cells within a mark may also increase, and is, therefore, only limited by the ability of the device to successfully read and process the information provided by the marks, and by the marking resolution capabilities of the laser and material. In some applications, such as anti-counterfeit applications, it may be preferable to design a small, e.g., microscopic, mark having a high cell count. In other applications, such as high-speed manufacturing lines, it may be desirable to have larger area marks that are easily perceptible for inspection and less complex with an optimal number of cells to minimize processing time.

As the area of the visible mark 16 increases, the size of each cell may also proportionally increase in size, so that a device, such as a smartphone, is capable of successfully reading and processing the information provided by the mark 16. The visible mark 16 may also be optimized by reducing the size of the cells within the visible mark 16 to allow for a maximum amount of information to be encoded while still being able to be recognized and processed successfully by the reading device. Preferred minimum cell sizes within a mark having a specified size are provided in Table 1.

TABLE 1

| Total Mark Size (mm) | Cell Size (μm) |
| --- | --- |
| 1.0 | 71 |
| 1.4 | 100 |
| 2.1 | 150 |
| 2.8 | 200 |

Figure 12A:
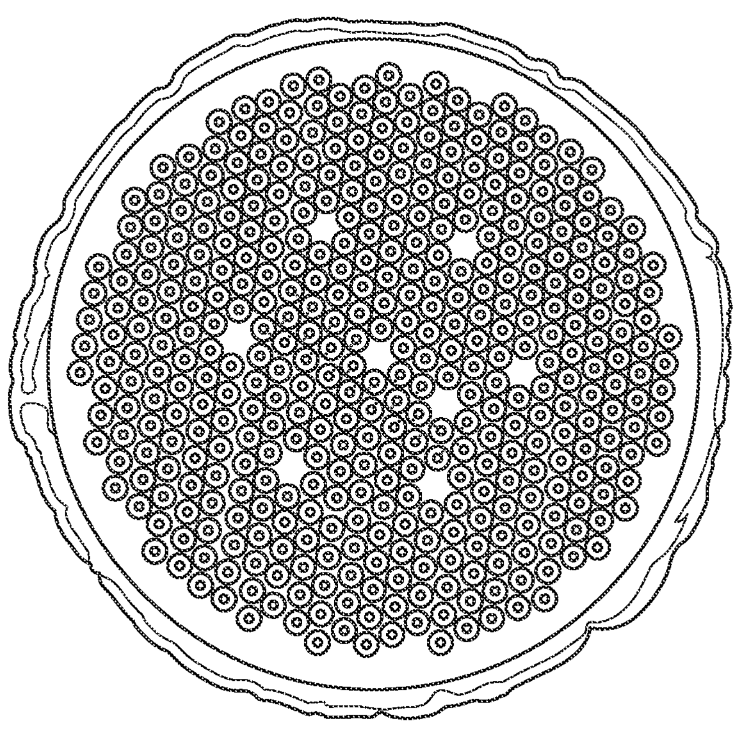
FIG. 12A is a top plan view of a molded panel containing a plurality of molded stoppers.
Figure 13:
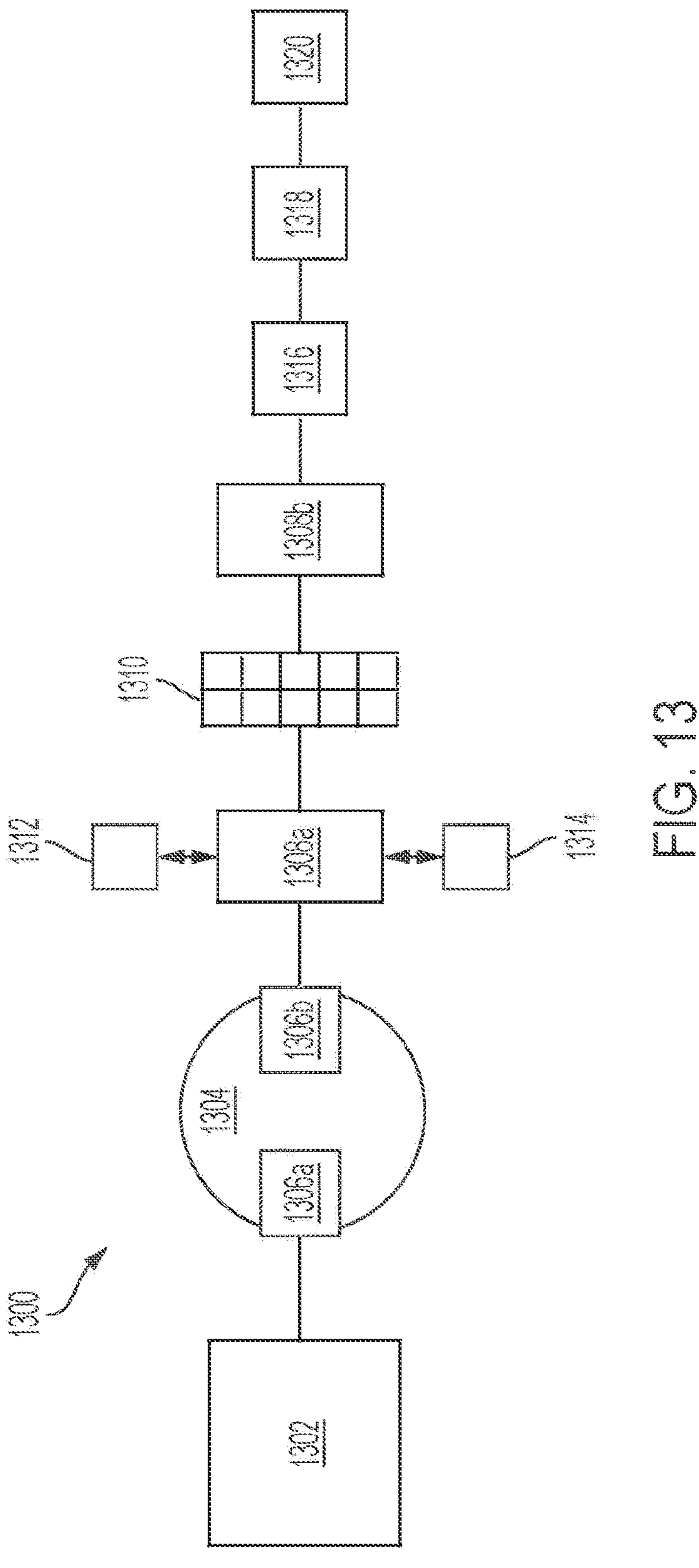
FIG. 13 is a plan schematic view of a system for manufacturing a plurality of elastomeric components having a surface mark according to another embodiment of the present invention.

According to one embodiment of the present invention, a system for manufacturing and marking a plurality of elastomeric components having a pre-applied film may be accomplished by using a laser that emits light at a wavelength for which the film is transparent. For example, a plurality of components in the form of stoppers may be manufactured in a first step by compression molding a sheet of elastomeric material to produce a panel, such as the molded panel of FIG. 12A. Referring to FIG. 13, a system for manufacturing the panel may include a mixing station 1302 that is configured to blend or compound the elastomeric material and optional additives for forming the elastomeric components. The mixing station 1302 may include one or more types of compounding equipment, such as Banbury mixers, extruders, etc. After the elastomeric material has been compounded, it may be delivered to a molding station 1304. According to a preferred embodiment, the molding station 1304 may be in the form of a carousel comprising a plurality of compression molds 1306*a*, 1306*b*. After delivering the elastomeric material into a first mold 1306*a* when the carousel is in a first position, the elastomeric material is compressed and then cured as the carousel rotates to a second position to form a pad containing a plurality of components, such as the pad of FIG. 12A. As the first mold 1306*a* is rotated to the second position, the second mold 1306*b* is rotated to the first position to receive elastomeric material from the mixing station 1302; thereby, providing a semi-continuous compression molding process. Examples of elastomeric components that may be molded within the pad include, but are not limited to, vial stoppers for containers containing liquid or lyophilized products and plungers for cartridges, syringes, or carpules. Each pad may comprise at least 50 components, more preferably at least 200 components, and most preferably at least 800 components. The pad may have a diameter of at least 10 cm, more preferably at least 20 cm, most preferably at least 30 cm. Either during or after the compression molding step, a polymeric film, such as ETFE, may be applied to one or more surfaces of the stopper.

After the pad has cured and the first or second mold 1306*a*, 1306*b* is in the second position, the mold opens and the pad is removed from the mold. The pad is preferably removed by an automated marking system having means to remove the pad from the mold. For example, in one embodiment, the automated marking system may comprise a robot 1308*a* that includes a mechanical arm configured to remove the pad from the mold. The automated marking system may further comprise a marking system 1312 that includes a laser for applying a mark to the surface of each component within the pad. For example, if the surface of the cured, untrimmed pad is coated with an ETFE film, a laser that emits light at a wavelength of 355 nm may be used to mark the surface of one or more stoppers because ETFE is transparent with respect to that particular wavelength of light. Thus, with reference to FIG. 2, the laser can be used to form the visible mark 16 on the body 12 even after an ETFE film 14 is formed thereon, as the radiation can pass through the film 14 without causing damage thereto. The film 14 has a transmittance at the laser wavelength (often a predetermined wavelength in the UV range) of, with increasing preference in the order listed, at least 5%, at least 10%, at least 20%, at least 30%, at least 40%, at least 50%, at least 60%, at least 70%, and at least 80%.

As previously discussed, the laser mark is preferably provided in the form of a Data Matrix ECC 200 code. More preferably the Data Matrix ECC 200 code is in the form of a square having a side length of about 1.4 mm and each cell within the mark has a maximum dimension of about 0.10 mm, more preferably about 0.08 mm. This will result in a 14×14 Data Matrix ECC 200 code capable of encoding a 16-digit serial number. The 16-digit serial number may be used to provide a unique identifier for each component within the pad, as well as source information. For example, in a preferred embodiment, the 16-digit serial number may be presented as follows:

YYDDDAABBXXXXXXX, wherein YY is the two-digit number indicating the year in which the component was made (e.g. "19" for the year 2019), DDD is a three-digit number indicating the day on which the component was made (e.g. "001" for January 1 or "365" for December 31), AA is a two-digit number that identifies the system used to manufacture the component, such as the system illustrated in FIG. 13, BB is a two-digit number that identifies the geographical location of system, and XXXXXXX is a seven-digit number associated with the specific component. By providing this information, it will enable an end-user or manufacturer to pinpoint the time and location associated with the origin of a specific component, which may be critical information in certain situations, such as a product recall, as will be described in greater detail below.

Figure 12B:
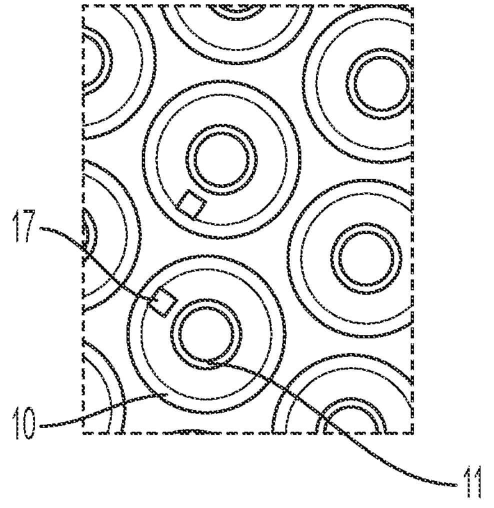
FIG. 12B is a magnified view of the top surface of the molded stoppers of FIG. 12A having a surface mark according to yet another embodiment of the present invention.

Referring to FIG. 12B, the marking 17 may be applied to the top surface of a stopper 10, preferably outside of a target area 11. The target area 11, bounded by a circle, identifies the area through which a syringe needle (not shown) should be inserted in order to extract the contents of a container (not shown) that is sealed with the stopper 10. The marking 17 is preferably outside of the target area to prevent potential contact between the contents of the container and the portions of the stopper 10 treated with the laser that formed the marking 17.

After each component on the pad has been laser marked, the robot 1308*a* may present the untrimmed, laser marked pad to an inspection station 1314. The inspection station 1314 may comprise one or more cameras configured to capture an image (e.g. a photograph or video) of each marking on the pad. For example in one embodiment, the robot 1308*a* may move the pad across the field of view of one or more stationary cameras within the inspection station 1314. Alternatively, the robot 1308*a* may present and maintain the pad in a stationary position while one or more cameras within the inspection station 1314 scan the laser markings. This may be accomplished by mounting the one or more cameras on a movable carriage. In another embodiment, both the pad and the one or more cameras may be moved simultaneously to increase the speed at which the images of the laser markings are captured. The inspection station 1314 may also be used to scan one or both sides of the pad to identify any defects in the components, for example.

The inspection station 1314 may further comprise a processor configured to identify the location of the marking on the surface of the component and/or read and record each serial number associated with the markings. By identifying the location of the marking on the surface of the component, the inspection station 1314 may confirm that the marking 17 has been applied outside the target area 11 and is readable, for example. If not, the component may be rejected and discarded later in the process. By recording the serial numbers of the components within the untrimmed pad, it may be easier to determine whether the source of any defects is associated with the mold. For example, after trimming and separating the components from the pad, the individual elastomeric components may be inspected to identify any physical defects. If a defect is identified, the serial number associated with the component may be recorded. If several defects are identified, the serial numbers may be compared to determine if the defect is occurring in elastomeric components that may be found in a common location on one or more of the molded pads prior to trimming. This may suggest that a root cause of the defects is found in one of the compression molds, e.g. 1306*a* or 1306*b*. The decoding and recording of the serial numbers associated with each component may be accomplished by the processor after the one or more images are captured and optionally after the pad has been removed from the inspection system 1314 and while the pad continues through the system 1300.

After formation and visual inspection of the markings 17 on each component of the pad, the robot 1308*a* may place the pad in a cooling system 1310. The cooling system 1310 may comprise a rack on which the pads may rest. The cooling system 1310 may further comprise other optional features, such as a climate-controlled cabinet, a dehumidifier, or cooling fans, for example. Once cooled, a second robot 1308*b* that is the same or similar to the first robot 1308*a* may remove the pad from the cooling system 1310 and deliver the pad to one more processes, such as a trimming station 1316 for removing each component from the molded panel by cutting or trimming the excess elastomeric material around each component using a blade or similar tool, as known by those of skill in the art, a washing station 1318 for cleaning and/or sterilizing the individual components, and a packing station 1320 configured to load a plurality of trimmed and washed components into a package, such as a bag or box. One or more additional inspection stations that are the same or similar to inspection station 1314 may be added to the system 1300 between trimming station 1316 and washing station 1318 and/or between the washing station 1318 and packing station 1320 to inspect and detect any defects in the components. As previously noted, the serial number of the defective component may be read and recorded prior to discarding the defective component.

As previously mentioned, it is preferred that certain embodiments of the inventions apply a film to the components that is made of a material that is substantially transparent to the type of laser light that will be used to apply a marking to the surface of the component. Optical microscopic observations, such as those shown in FIGS. 4A and 4B, have demonstrated that no visible degradation to the film 14 may be generated by the laser. Various types of lasers may be paired with various polymer films or covers (e.g., polypropylene or fluorinated ethylene propylene (FEP) caps or the like) that are essentially transparent to the respective wavelength to accomplish the same result, i.e. the formation of a visible mark on the surface of the component and underneath a pre-applied film or cover. As a result of this effect, creation of the visible mark 16 can occur any time after molding of the stopper 10, allowing inclusion of additional data throughout the manufacturing process while minimally impacting current manufacturing processes. Visible marks 16 have also been shown to withstand steam sterilization temperatures (e.g., up to 121° C.) for various materials.

Figure 10A:
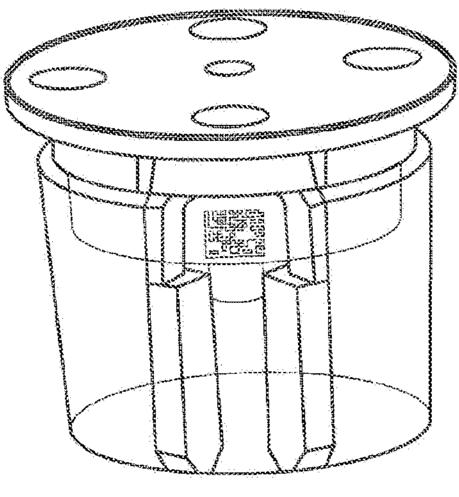
FIG. 10A is a top perspective view of an elastomeric stopper having surface marks assembled in a closure with a transparent cap according to another embodiment of the present invention.
Figure 10B:
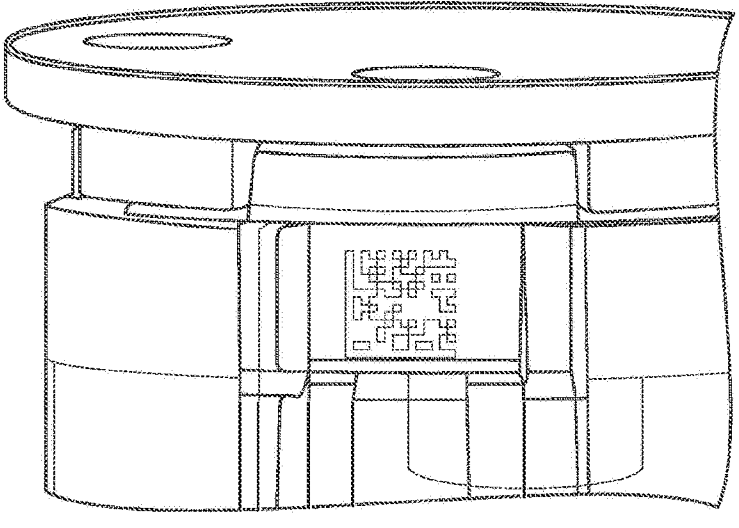
FIG. 10B is a magnified view of one of the surface marks in the assembly of FIG. 10A.
Figure 11:
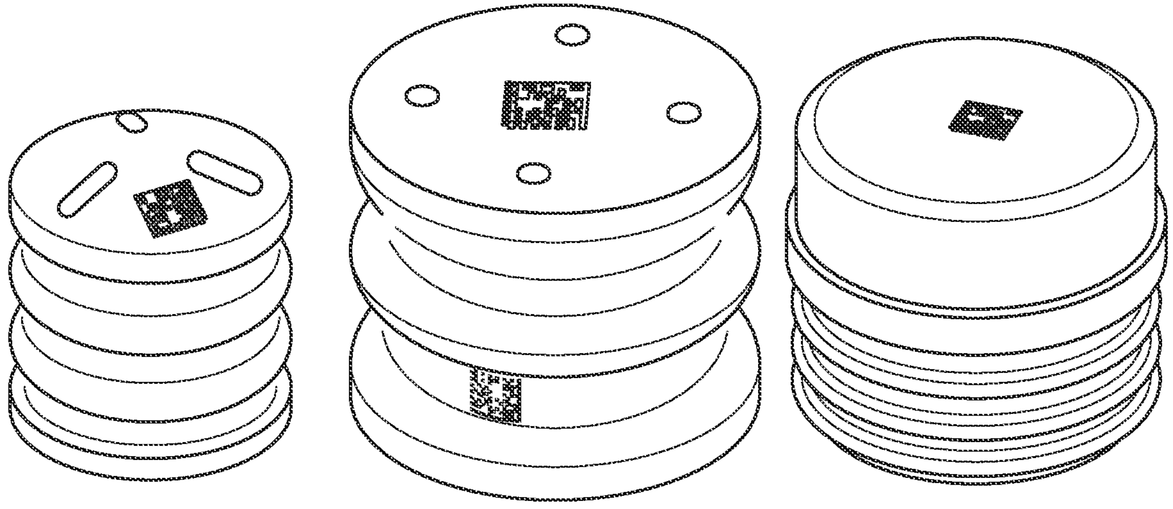
FIG. 11 is top perspective view of various elastomeric plungers having surface marks according to yet another embodiment of the present invention.

For some methods according to the various embodiments of the present invention, the marking may be applied to the component after the component has been incorporated into an assembly. For example, an elastomeric stopper may be incorporated into a transparent cap, such as the DAIKYO PLASCAP® RUV closures manufactured by Daikyo Seiko Ltd. Upon selection of an appropriate transparent material for the cap and a corresponding wavelength of light emitted by the laser, such that the light will be substantially transmitted through, rather than absorbed by, the cap and film, a marking may be applied to the surface of the elastomeric stopper after being assembled in the transparent cap (FIGS. 10A and 10B). Similarly, in another example, the surface of various types of elastomeric plungers (FIG. 11) may be marked with an appropriate wavelength laser either before or after the plunger is inserted into a transparent syringe or cartridge barrel. Again, a wavelength of light should be selected, such that the light is not substantially absorbed by the transparent material (e.g., glass, polymeric material, or the like) of the cartridge or syringe barrel.

Figure 5:
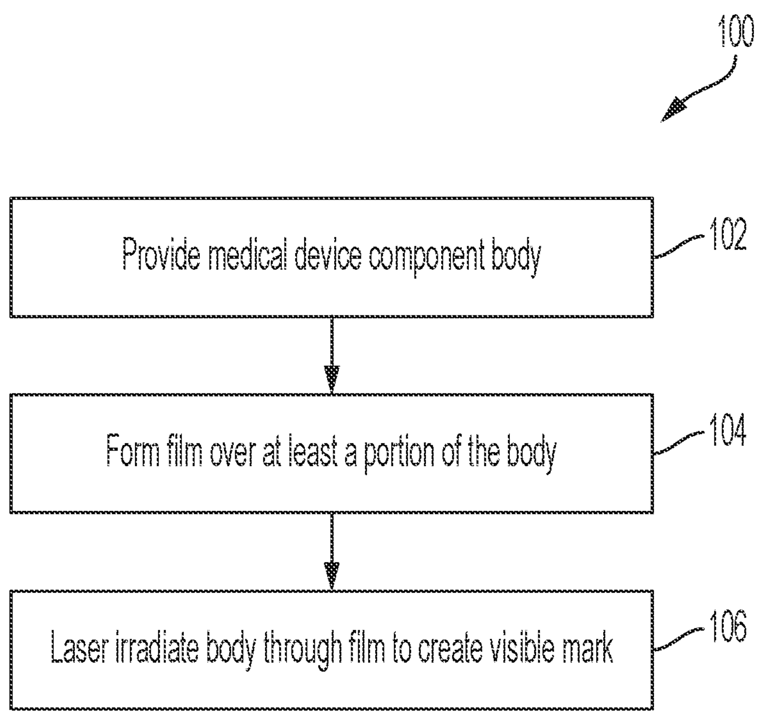
FIG. 5 is a schematic flow chart of an exemplary method of manufacturing a stopper in accordance with another embodiment of the present invention.

FIG. 5 shows one exemplary method 100 for manufacturing a medical device components, such as a stopper 10. At step 102, a body 12 may be provided having a surface and being at least partially formed from the markable material, such as the rubber with inorganic filler materials described above. The body 12 may be molded according to conventional techniques. At step 104, a film 14, such as the ETFE described above, may thereafter be formed to cover at least a portion of the surface of the body 12, and includes covering at least a portion of the markable material (e.g., where the body 12 may be formed partially of the markable material and partially of some other material designed for structural support and/or aesthetics).

At step 106, after the film 14 is formed, the visible mark 16 may be formed on the surface of the body 12 covered by the film 14 by exposing one or more areas of the markable material to laser irradiation of a predetermined wavelength (such as in the UV wavelength range), thereby changing the color of the exposed areas. This exposure can include, for example, rastering the laser irradiation across a plurality of areas on the body 12 to form spatially extending visible marks 16 (e.g., the machine readable code in FIGS. 1-4B) and/or a plurality of visible marks 16 (e.g., visible marks 16*a*-16*d* in FIG. 7).

In one aspect, it is desirable to be able to incrementally add information to a medical device component, such as the stopper 10, throughout the manufacturing process. This can be done by, for example, adding additional data matrix codes, or by extending an already present visible mark 16 (i.e., adding more symbols or characters).

Figure 6:
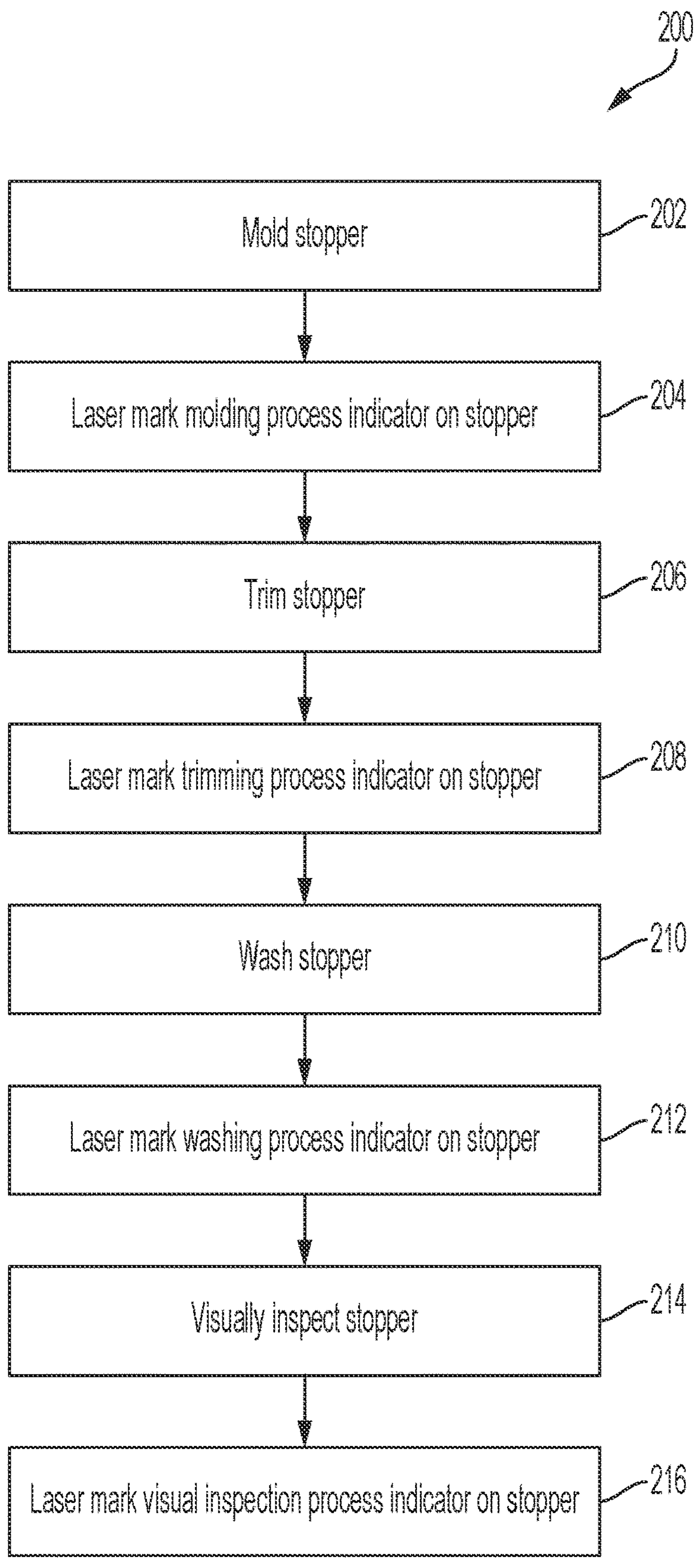
FIG. 6 is a schematic flow chart of an exemplary method of manufacturing and serially marking a stopper in accordance with yet another embodiment of the present invention.

FIG. 6 shows one example of a portion of a manufacturing process 200 for the stopper 10 in this manner. At step 202, the stopper 10 is molded in a conventional manner, which preferably includes application of the film 14 in appropriate locations. At step 204, the stopper 10 is laser marked in a first area of the body 12 with a molding process indicator before it is moved to the next process. The molding process indicator, and other similar process indicators, may be a coded mark (similar to the visible mark 16 in FIGS. 1-4B) containing data (e.g., a time stamp, parameter information related to the molding process, or the like) or a unique ID or URL linking to an updatable database in which information related to completed process steps, like molding, can be identified and described. Alternatively, the molding process indicator can be a graphical symbol representing that the molding step has been completed (e.g., the visible mark 16*a* in FIG. 7), or other like marks.

At step 206, the stopper 10 is trimmed from its mold and at step 208, a trimming process indicator is formed on the stopper 10 in a second area of the body 12 through laser marking (see e.g., the visible mark 16*b* in FIG. 7). At step 210, the stopper 10 is washed in a conventional process. At step 212, the stopper 10 is laser marked in a third area of the body 12 with a washing process indicator (see e.g., the visible mark 16*c* in FIG. 7). At step 214, the stopper 10 may be visually inspected for defects, either manually or by an inspection machine. At step 216, a visual inspection process indicator is laser marked in a fourth area of the body 12 onto the stopper 10 (see e.g., the visible mark 16*d* in FIG. 7). Where the visible mark 16 is a machine-readable code that is added onto following each relevant process, the various marking areas can be adjacent to one another, or each step may invoke its own separate and independent code. While various process steps are shown in FIG. 6, and each is followed by a laser-created process indicator, the illustrated process is not limiting and variations in the steps, the number of laser-created process indicators, and the like can be made without departing from the spirit and scope of the present invention.

The above-described process is beneficial in that the need for a server query or operation during a manufacturing process can be removed. A high-speed filling line does not tolerate significant latency, and while the visible mark 16 can store limited data, there is no latency in retrieval, and can therefore be implemented on a high speed line.

In certain embodiments, the visible mark 16 can be used for unique serialization. As briefly described earlier, after each processing step, a database (not shown) may be updated with information related to the unique identifier (e.g. serial number) associated with the visible mark 16 of each stopper 10. For example, once a batch of elastomeric components has been tested for quality parameters, such as particulates, extractables and leachables, the laser marking on each component may be scanned and decoded, and the database may be populated with the data after each test, such that those data are associated with each serial number within the database. A time stamp and metadata can be appended to entry for the specific visible mark 16 in a table as the component is scanned at each step. In one embodiment, the visible mark 16 can include a short URL, or unique ID, and each component can point to a manufacturer controlled website, API, or database with a log where individuals can retrieve data or metadata associated with the component (e.g., lot/batch information, process parameter information, drug safety details, interaction details, administration details, recall information, expiration dates, and the like). Components can then be tracked by geography, time, users, and the like. Drug manufacturers, pharmacies, healthcare providers and the like may also be allowed to add information associated with the particular component.

With this process, information can be used to, for example, find defective mold cavities, identify where waste is being generated in a manufacturing system, provide traceability, assign unique patient IDs for emerging cell therapies, or to inform a patient about every person who enabled their treatment. The database can, in some instances, be pre-fetched prior to device manufacturing (for example, if a plurality of stoppers are all already uniquely marked) in order to reduce lag.

The process also serves as anti-counterfeit means. By tracking each component, identification and prevention of the re-use of components is achievable where serialization is copied. It may also be desirable to prevent a hostile third party from predicting serial numbers. To prevent such activity, a visible mark 16 may contain encrypted information that can only be read by the customer. For example, the visible mark 16 may include a digital signature. As understood by those of skill in the art, the data encoded in visible mark 16 may be digitally signed. The end user can then confirm the authenticity of the message and therefore the component. Various other one-way hash, or cryptographic authentication methods (e.g., Pretty Good Privacy (PGP) encryption or the like) can also be used to verify that messages in the visible mark 16 actually come from the component manufacturer and optionally protect those messages. Depending on the application, cryptographic keys may be used differently. In one example, the manufacturer may choose to encrypt a message with their private key, so that all authorized users may decrypt and verify the message. In another example, messages for a specific customer could be encrypted with the customer's public key, so that only the specific customer could decrypt the message.

The process can also serve to serialize components to be tracked together as part of one medical device. For example, each component may have one or more visible marks 16 that can be related to one another in the database. In this manner, manufacture, sale, shipping, and usage of an entire device can be tracked, and be correlated to individual components. For example, if the visible mark 16 on the stopper 10 does not correlate with the visible mark on one of the other device components, early detection of either improper manufacture or the use of counterfeit components may be detected. Similarly, recalls of particular components can be easily traced to devices in which those components are incorporated. In another embodiment, a single one of the components may include a laser-created visible mark 16, which then serves to link to a database for which all subsequent device information (e.g., manufacturing details, drug information, gene therapy information, patient information, expiration date, serial number) and the like can be stored and tracked. Patient information may include the patient's identity, intended treatment schedule, treatment administration information (e.g., frequency and type of medical therapy/device used), and any other patient metadata, so that the visible marking 16 may be used by a system that includes a personalized treatment application. The personalized treatment application may be available on a system, such as an electronic device, e.g., smartphone, tablet, laptop, or the like.

Similarly, entire shipments of components can be tracked and manufacturing information may be maintained by tying visible marks 16 together in the database. For example, a bag may contain a plurality of stoppers 10 each having an individual serial number in the form of a laser-created visible mark. Those serial numbers may be associated with one another in the database. In one exemplary operation, when the bag undergoes sterilization, the data for each stopper 10 in the bag can be updated either by scanning a tag on the bag affiliated with the stopper 10 serial numbers, or by scanning the visible mark 16 of one of the stoppers 10 and using previously established links to update the remaining stopper data.

While the above embodiments illustrate a single visible mark 16 or describe a series of similar visible marks (e.g., multiple data matrix codes or graphical symbols), multiple visible marks of different characteristics may also be applied to the components. For example, one visible mark 16 may contain the relevant manufacturing data, while a second visible mark 16 may be a logo of the manufacturer. Other types of visible marks, such as visual indicators to caregivers, such as a location for needle insertion, can be used as well.

Figure 8A:
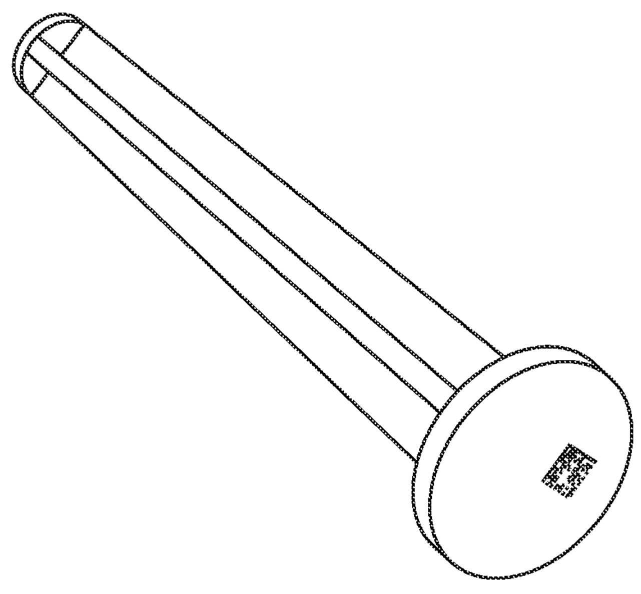
FIGS. 8A and 8B are top perspective views of a plunger rod having surface marks according to another embodiment of the present invention.
Figure 8B:
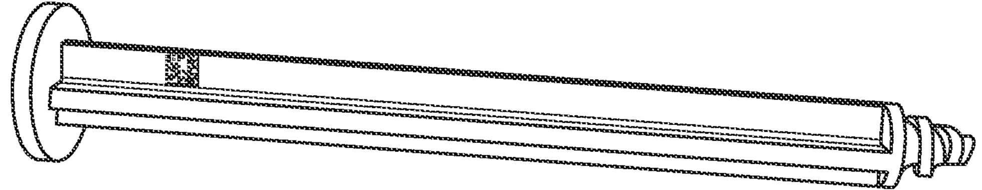
Figure 9A:
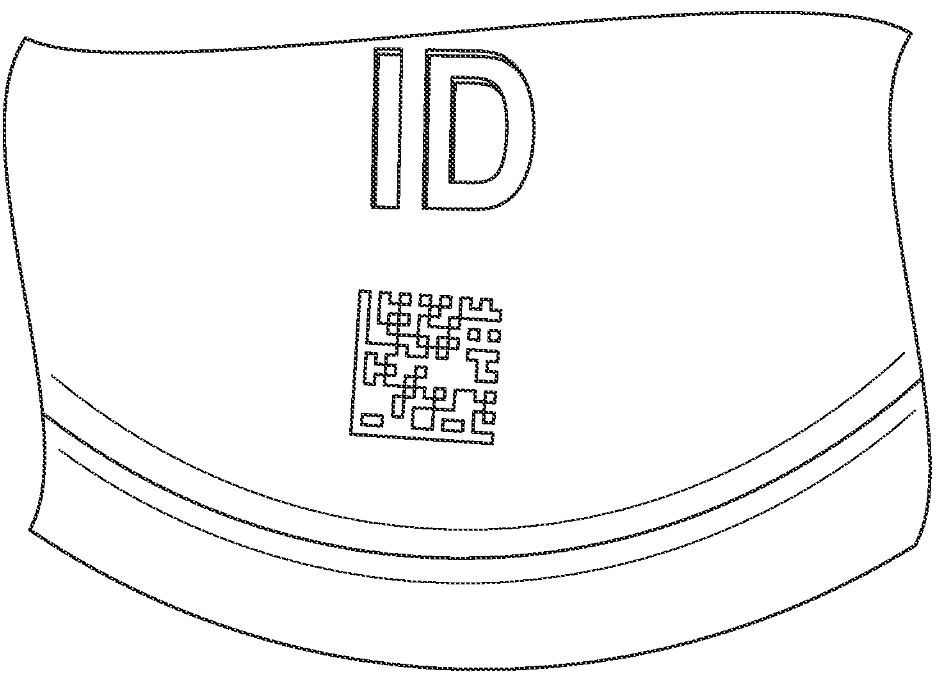
FIG. 9A is a top plan magnified view of a plastic cap of a seal having a surface mark according to another embodiment of the present invention.
Figure 9B:
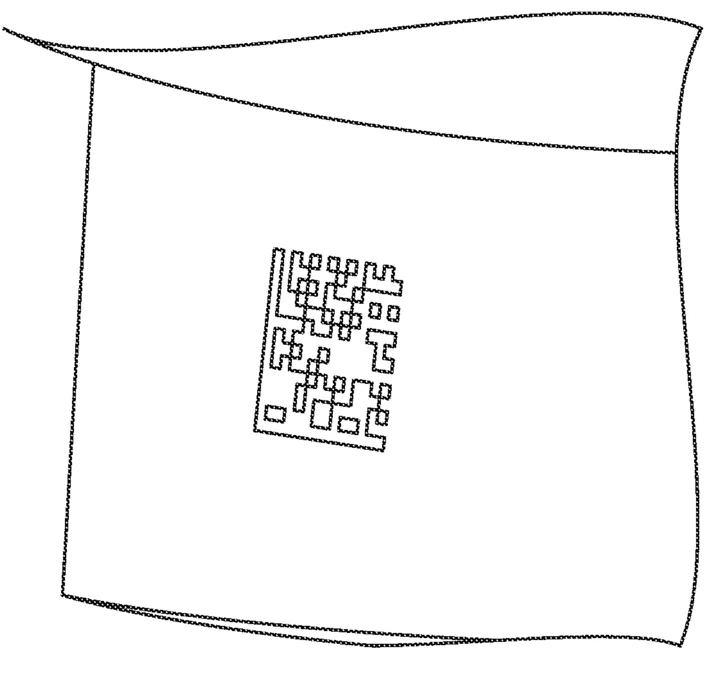
FIG. 9B is a side magnified view of an aluminum seal having a surface mark according to another embodiment of the present invention.

While the above embodiments have been discussed in relation to elastomeric medical device components, laser marking in accordance with the invention can be utilized in other medical device components as well. For example, the laser marking may be applied to one or more surfaces of a plunger rod (FIGS. 8A and 8B) either before or after the plunger rod is inserted into a transparent syringe barrel. In another example, aluminum seals having plastic flip-top caps may be marked, either by marking the top surface of the plastic cap or by marking a pigmented lacquer containing $TiO_2$ formed on the aluminum sidewall or by marking the aluminum itself through a clear lacquer (FIGS. 9A and 9B). Plastic seals and other pigmented plastics, as well as line seals produced from elastomer sheeting, are compatible with the laser marking process. Glass components can be laser marked, as can glass substitute components, such as those made using CRYSTAL ZENITH® material manufactured by Daikyo Seiko, Ltd of Japan, using $CO_2$ lasers or the like to burn and/or ablate material.

While specific and distinct embodiments have been shown in the drawings, various individual elements or combinations of elements from the different embodiments may be combined with one another while in keeping with the spirit and scope of the invention. Thus, an individual feature described herein only with respect to one embodiment should not be construed as being incompatible with other embodiments described herein or otherwise encompassed by the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the disclosure herein.

We claim:

1. A system for manufacturing elastomeric components, the system comprising:

a molding station comprising a mold, the molding station being configured to receive an elastomeric material, to form a pad comprising a plurality of untrimmed elastomeric components, and to cure the pad;

an inspection station comprising a processor and a camera; and an automated marking station comprising a laser, the automated marking station being configured to remove the cured pad from the molding station, to present the cured pad to the laser to form a mark on each of the untrimmed elastomeric components, and to present the cured pad to the inspection station to capture an image of each mark with the camera, wherein the processor is configured to determine a location of each mark on the elastomeric components, to determine that the location of the mark on one of the elastomeric components is not outside of a target area, and to reject the one of the elastomeric components based on the location of the mark on one of the elastomeric components not being outside of the target area.

2. The system of claim 1, further comprising a mixing station configured to compound the elastomeric material and deliver the elastomeric material to the molding station.

3. The system of claim 1, wherein the molding station comprises a plurality of compression molds.

4. The system of claim 1, wherein the mark is a data matrix code.

5. The system of claim 1, wherein the processor is configured to decode each mark and record a unique identifier associated with each mark.

6. The system of claim 1, further comprising a cooling station configured to receive the cured pad following application of the mark to each untrimmed elastomeric component.

7. The system of claim 6, further comprising a robot configured to remove the cured pad from the cooling station and to deliver the cured pad to at least one of a trimming station, a washing station, or a packing station.

8. The system of claim 7, further comprising a second camera configured to capture a second image of the mark of at least one of the elastomeric components following processing by at least one of the trimming station or the washing station.

9. The system of claim 1, wherein the processor is configured to determine whether each mark on the elastomeric components is readable.

10. The system of claim 9, wherein the processor is configured to determine that the mark on one of the elastomeric components cannot be read, and the system is configured to reject the one elastomeric component based on the determination that the mark on the one elastomeric component cannot be read.

11. The system of claim 1, further comprising a trimming station configured to trim the pad to separate the elastomeric components after the image is captured.

12. The system of claim 1, wherein the automated marking station comprises a robot configured to remove the cured pad of untrimmed elastomeric components from the molding station.

* * * * *